(12) United States Patent
Chen

(10) Patent No.: US 9,289,588 B2
(45) Date of Patent: Mar. 22, 2016

(54) CONNECTOR AGAINST CONTRARY FLOWING FOR MEDICAL TREATMENT

(71) Applicant: YI-JIN PROMOLD ENTERPRISE LTD., New Taipei (TW)

(72) Inventor: Chin-Yi Chen, New Taipei (TW)

(73) Assignee: YI-JIN PROMOLD ENTERPRISE LTD., New Taipei (TW)

( * ) Notice: Subject to any disclaimer, the term of this patent is extended or adjusted under 35 U.S.C. 154(b) by 60 days.

(21) Appl. No.: 14/492,688

(22) Filed: Sep. 22, 2014

(65) Prior Publication Data

US 2015/0102245 A1    Apr. 16, 2015

(30) Foreign Application Priority Data

Oct. 16, 2013 (TW) .............................. 102219299 U

(51) Int. Cl.
*F16L 37/28* (2006.01)
*A61M 5/14* (2006.01)
*A61M 39/10* (2006.01)
*A61M 39/26* (2006.01)
*A61M 39/24* (2006.01)

(52) U.S. Cl.
CPC ............... *A61M 39/10* (2013.01); *A61M 39/26* (2013.01); *A61M 2039/1033* (2013.01); *A61M 2039/2433* (2013.01); *A61M 2039/266* (2013.01); *A61M 2039/267* (2013.01)

(58) Field of Classification Search
CPC .......... A61M 39/26; A61M 2039/266; A61M 2039/267

USPC ................ 604/30, 33, 82, 83, 89, 91, 167.03, 604/170.01, 187, 188, 236, 237, 247, 249, 604/256, 411, 414, 513, 523, 533, 534, 535, 604/536, 537, 538, 539, 905; 251/149.1, 251/149.6, 149.7, 149.8; 137/843, 859, 137/601.3

See application file for complete search history.

(56) References Cited

U.S. PATENT DOCUMENTS

| | | | | |
|---|---|---|---|---|
| 5,549,566 | A * | 8/1996 | Elias | A61M 39/045 604/167.03 |
| 6,050,978 | A * | 4/2000 | Orr | A61M 39/26 251/149.1 |
| 6,079,432 | A * | 6/2000 | Paradis | A61M 39/26 137/1 |
| 7,914,502 | B2 * | 3/2011 | Newton | A61M 39/045 604/246 |
| 9,192,753 | B2 * | 11/2015 | Lopez | A61M 39/10 |

* cited by examiner

*Primary Examiner* — Mary McManmon
*Assistant Examiner* — Hailey K Do
(74) *Attorney, Agent, or Firm* — Bacon & Thomas, PLLC

(57) ABSTRACT

A connector against contrary flowing for medical treatment, as to its structure, it includes a connecting seat to connect with a transmitting pipe, an insertion connecting cap fixed on the connecting seat for insertion of an external connecting terminal and a needless injection cylinder, and an elastic valve plug provided between the connecting seat and the insertion connecting cap, when the injection cylinder is pulled out of the insertion connecting cap, the elastic valve plug can impede the reverse pressure generated by the transmitting pipe (or the connecting seat), in order to avoid generating reverse flow of blood of a patient to reduce pain.

9 Claims, 12 Drawing Sheets

CONNECTOR AGAINST CONTRARY FLOWING FOR MEDICAL TREATMENT

BACKGROUND OF THE INVENTION

1. Field of the Invention

The present invention relates to a connector, and especially to a connector against contrary flowing for medical treatment, the connector is installed on a medical equipment, such as an upper lid of a liquid transmission measuring cylinder, a pipe line for sampling of a specimen, a pipe line for intravenous injection etc., they can be used to input liquid medicine (adding medicine), sampling, or for use of an air inflation type respirator etc. after an external connecting terminal or a needless injection cylinder is inserted therein.

2. Description of the Prior Art

A connector for medical treatment is applied in various equipments, such as a pipe line for sampling of a specimen, a pipe line for intravenous injection, an upper lid of a liquid transmission measuring cylinder, and an air inflation type respirator etc., they can be used to be expedient for personnel in doing medical treatment of curing patients and sampling specimens, and can reduce rate of infection in using of syringe needles and production of waste materials in medical treatment. Conventional connectors each includes a connecting seat with a flowing channel, an insertion connecting cap for insertion of an outer liquid transmission pipe installed on the connecting seat, and an elastic valve plug provided between the connecting seat and the insertion connecting cap for keeping the sealed state of the connecting seat.

Take a pipe line for intravenous injection as an example, when a patient uses a dropping bottle, one of medical treatment personnel will insert an input syringe needle into a vein of the patient, the pipe line on the rear end of the input syringe needle is insertion connected with the connecting seat of the connector; when in use, the liquid transmission pipe of the dropping bottle is inserted into the insertion connecting cap, the elastic valve plug can be pressed to open the flowing channel of the connecting seat, in order that the dropping bottle injects the medicament into the body of a patient through the liquid transmission pipe, the connector and the input syringe needle, at the time the injection is finished or is temporarily stopped, it needs only to pull out the liquid transmission pipe, then the elastic valve plug is automatically restored to its original position to seal the connecting seat, this can avoid the danger of contrary flowing of blood, and the patient can move about freely, if a second time injection and dropping is required, it needs only to insert the liquid transmission pipe into the insertion connecting cap of the connector, and injection of the medicament can be continuous, this can eliminate the inconvenience of the patient in repeatedly doing injections.

Additionally, in order that the flowing rate of the dropping bottle is under control, normally a liquid transmission measuring cylinder on the dropping bottle for flowing rate controlling is installed on the liquid transmission pipe. And partial of the patients probably still need to be injected with other medicaments in addition to be dropping injected, hence an upper lid of the liquid transmission measuring cylinder may be installed additionally with a connector, the passage of the connecting seat of the connector is communicated with the inner space of a quantitative cylinder, so that the medical personnel can take advantage of a needless injection cylinder loaded with other medicament to insert it into a insertion connecting cap, in order to press the insertion connecting cap to open the flowing channel of the connecting seat for injecting medicament into the liquid transmission pipe, so that the medicament added can be injected together with the original medicament injected in the dropping bottle into the body of a patient.

Similarly, if the connector is provided on a pipe line for sampling of a specimen, it can be put into effect with a three-way pipe, thus the medical personnel can directly use the needless injection cylinder for inserting into the connector to extract the specimen, thereby infection rate of the patient can be lowered.

However, the conventional elastic valve plug of the connector has a defect of having an inferior efficiency of sealing, thereby when the liquid transmission pipe or the needless injection cylinder is pulled out, the flowing channel of the connecting seat will generate reverse pressure to render blood or medicament to contrarily flow back to the connector in a negative pressure mode, and thus increases the danger of repeatedly infecting. For instance, the techniques U.S. Pat. No. 8,152,790 B2, TW1378806, TWM279350 etc. do improvement on the efficiency of sealing of the elastic valve plug; it mainly increases the components for assembling of the elastic valve plug to strengthen the efficiency of sealing of the connector; however, the components of these techniques are relatively too many, their processes of assembling are also too complicated, thereby their costs of production are unable to be lowered effectively.

In view of the above, the inventor of the present invention provides a connector against contrary flowing for medical treatment based on his experience in study and practice, for the purpose of resolve the problems that the air tight effect of the elastic valve plug is inferior, and assembling of the components is complicated.

SUMMARY OF THE INVENTION

The object of the present invention is to provide a connector against contrary flowing for medical treatment, it is mainly to improve a sealing structure of a elastic valve plug, and to effectively impede generating of contrary flowing of a connecting seat by using a pressure balance principle to thereby avoid contrary flowing of blood or medicament, and to get the object of generating better air tight effect with least components.

In order to get the above object, the connector against contrary flowing for medical treatment of the present invention includes:

a connecting seat, the connecting seat has a hollow on its top, the hollow has at its center an upwardly protruding conical syringe needle, and the lower area of the hollow is extended downwardly to form a pipe connecting terminal to connect with a transmitting pipe; the top lateral wall of the conical shaped syringe needle is provided at least with an open hole, and has in it a transmitting channel getting downwards through the bottom of the pipe connecting terminal;

an elastic valve plug in a conical shape covering a conical shaped syringe needle, the elastic valve plug includes a fixed sheet provided at the bottom of the hollow, a pressed portion in the shape of having continuous waves extended upwards from the fixed sheet and surrounding the top outer periphery of the conical shaped syringe needle, a sealed portion extended upwards from the pressed portion and tightly contact the outer periphery of the conical shaped syringe needle, and a first stop annulus provided on the top outer periphery of the sealed portion having an outer radius larger than that of the sealed portion;

an insertion connecting cap fixed on the upper portion of the connecting seat, the insertion connecting cap has an annular connecting portion engaged with the inner periphery of the hollow of the connecting seat, a cavity for placing therein of the conical shaped syringe needle and being provided on the inner periphery of the connecting portion, the insertion connecting cap is provided on its top with an injection port connecting with the cavity, the radius of the injection port is smaller than that of the cavity and is provided at a mutual crossing area with the cavity with a stop wall, the above mentioned first stop annulus of the elastic valve plug is abutted against the stop wall to get an air tight state;

after a needless injection cylinder is inserted into the injection port of the insertion connecting cap, it can squeeze the elastic valve plug to make the sealed portion of the elastic valve plug press the pressed portion downwards to reveal the opening of the conical shaped syringe needle, thus the needless injection cylinder can get through the opening, the transmitting channel and the pipe connecting terminal, to make out putting from the transmitting pipe or absorbing the medicament, air or specimen; the character of it is resided in:

the inner periphery of the elastic valve plug and the outer periphery of the conical shaped syringe needle have between them a first gap, the bottom of the fixed sheet is provided around it with a downwardly protruding flange, thereby a second gap is formed between the center of the fixed sheet and the hollow of the connecting seat to connect with the above mentioned first gap, and the fixed sheet is provided thereon at least with a through hole making communication between the second gap and the cavity; the needless injection cylinder is to be pulled out of the injection port for restoring of the elastic valve plug to its original position, the reverse pressure generated by the pipe connecting terminal of the connecting seat can get through the transmitting channel, the opening, the first gap, the second gap and a couple of through holes, after that, enters the cavity of the insertion connecting cap to increase the inner pressure of the cavity, and then to presses the sealed portion of the elastic valve plug to tightly nestle to the outer periphery of the conical shaped syringe needle to resist the reverse pressure.

In comparison with the conventional technique, the tightly sealing structure of the present invention takes advantage of the pressure balance principle to effectively impede the reverse pressure generated by the connecting seat, in order to avoid contrary flowing of blood and the medicament to resolve the problems that the air tight effect of the elastic valve plug is inferior, and assembling of the components is complicated, and to get the object of generating better air tight effect with least components.

In view of the above stated, the present invention will be apparent in the followings description of technical measures after reading the detailed description of the preferred embodiments thereof in reference to the accompanying drawings.

DETAILED DESCRIPTION OF THE PREFERRED EMBODIMENT

Figure 1:
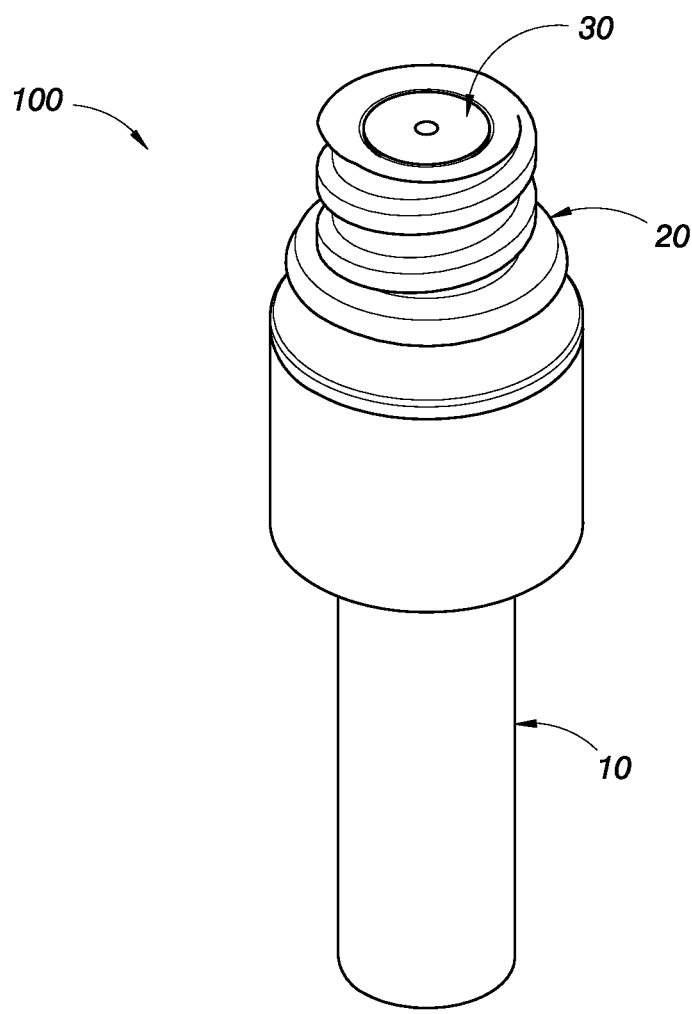
FIG. 1 is a perspective view of the present invention.
Figure 2:
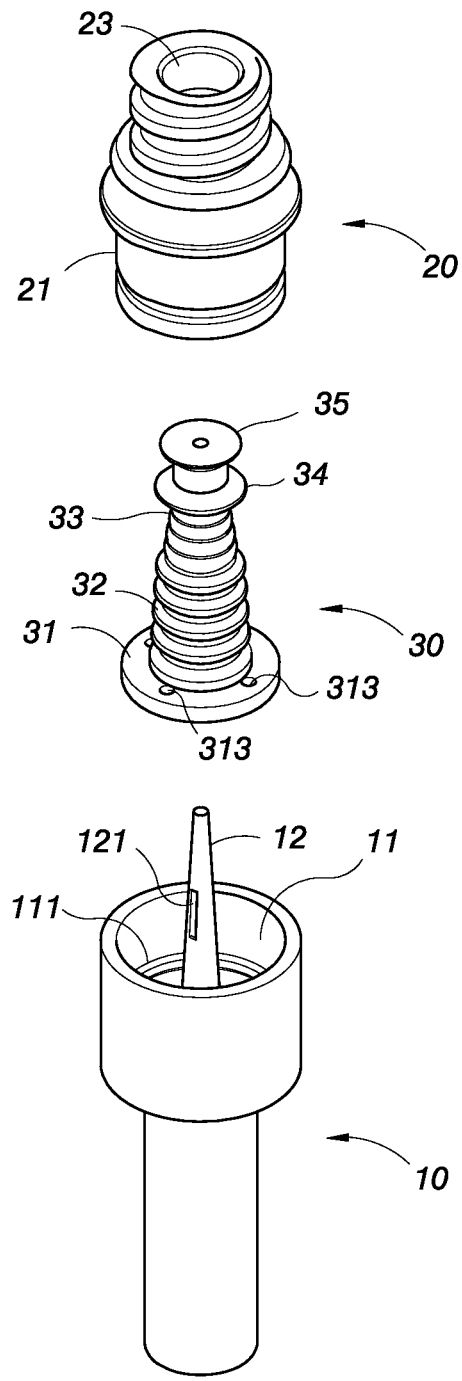
FIG. 2 is an analytic perspective schematic view of the present invention.

Referring to FIGS. 1 and 2, the connector 100 against contrary flowing for medical treatment of the present invention includes: a connecting seat 10, an insertion connecting cap 20 provided on the connecting seat 10 for insertion therein of a needless injection cylinder, and an elastic valve plug 30 provided between the connecting seat 10 and the insertion connecting cap 20 to keep a sealed state of the connecting seat 10.

Figure 3:
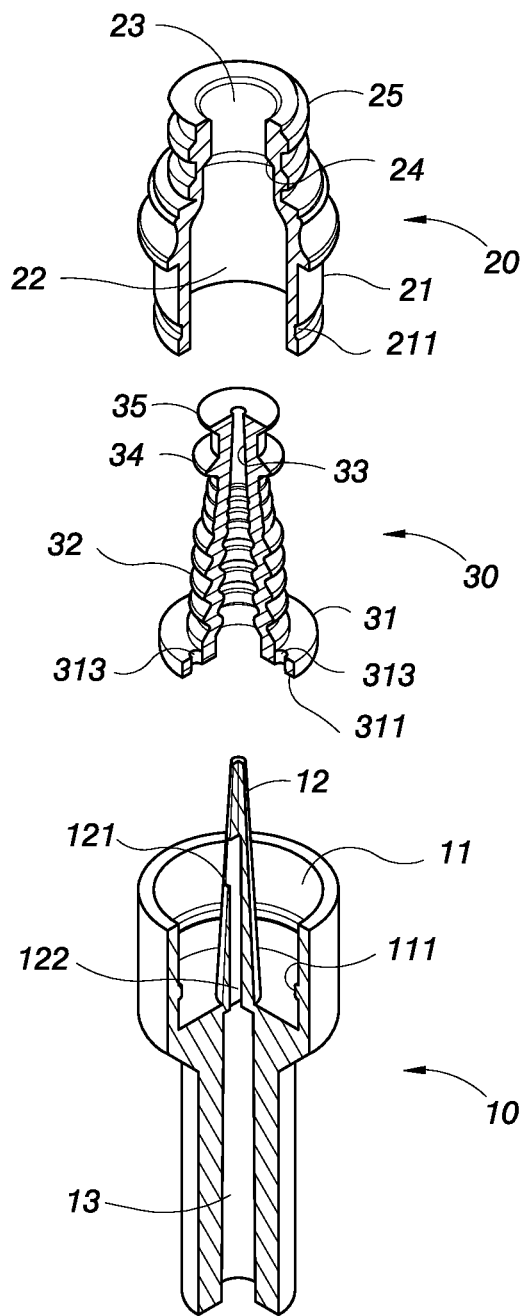
FIG. 3 is a perspective and partial sectional view of the present invention.
Figure 4:
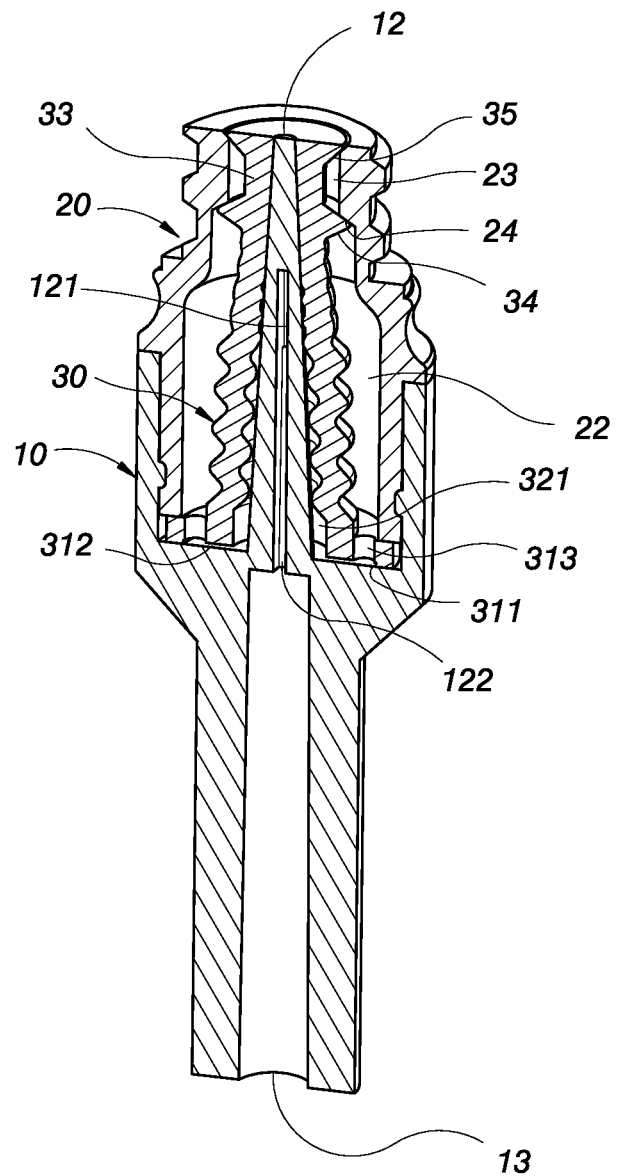
FIG. 4 is a schematic sectional view showing the assembly of the present invention.

Referring to FIGS. 3 and 4, the connecting seat 10 has a hollow 11 on its top, the hollow 11 has at its center an upwardly protruding conical syringe needle 12, and the lower area of the hollow 11 is extended downwardly to form a pipe connecting terminal 13 to connect with an outer transmitting pipe; the top lateral wall of the conical shaped syringe needle 12 is provided at least with an open hole 121, and has in it a transmitting channel 122 getting downwards through the bottom of the pipe connecting terminal 13.

An elastic valve plug 30 which is in a conical shape covering a conical shaped syringe needle 12, and includes a fixed sheet 31 provided at the bottom of the hollow 11, a pressed portion 32 in the shape of having continuous waves extended upwards from the fixed sheet 31 and surrounding the outer periphery of the conical shaped syringe needle 12, a sealed portion 33 extended upwards from the pressed portion 32 and tightly contact the top outer periphery of the conical shaped syringe needle 12, and a first stop annulus 34 provided on the outer periphery of the sealed portion 33 having an outer radius larger than that of the sealed portion 33.

The inner periphery of a pressed portion 32 of the elastic valve plug 30 and the outer periphery of the conical shaped syringe needle 12 have between them a first gap 321, the bottom of the fixed sheet 31 is provided around it with a downwardly protruding flange 311, thereby a second gap 312 is formed between the center of the fixed sheet 31 and the hollow 11 of the connecting seat 10 to connect with the above mentioned first gap 321, and the fixed sheet 31 is provided thereon at least with a couple of through holes 313 making communication between the second gap 312 and a cavity 22 in the inner side of the insertion connecting cap 20.

The above mentioned insertion connecting cap 20 is fixed on the upper portion of the connecting seat 10, and the insertion connecting cap 20 has an annular connecting portion 21 engaged with the inner periphery of the hollow 11 of the connecting seat 10, the cavity 22 is located at the inner periphery of the connecting portion 21 for receiving the conical shaped syringe needle 12, the insertion connecting cap 20 is provided on its top with an injection port 23 connecting with the cavity 22 for insertion therein of the above mentioned needless injection cylinder, the radius of the injection port 23 is smaller than that of the cavity 22 and is provided at a mutual crossing area with the cavity 22 with a stop wall 24, the above mentioned first stop annulus 34 of the elastic valve plug 30 is abutted against the stop wall 24 to get an air tight state.

Further, the sealed portion 33 of the elastic valve plug 30 is provided with a second stop annulus 35 corresponding by position to the inner periphery of the opening of the injection port 23 and having a radius larger than that of the sealed portion 33, the second stop annulus 35 can increase the air tight effect of the elastic valve plug 30 against the connecting seat 10.

And more, the insertion connecting cap 20 is provided on the outer periphery of the annular connecting portion 21 with a positioning annular recess 211 or an external screw thread, the inner periphery of the hollow 11 of the connecting seat 10 is provided at a position corresponding to that of the positioning annular recess 211 or an outer screw thread with a positioning protruding annulus 111 or an inner screw thread; it is shown in the drawings and taking the positioning protruding annulus 111 and the positioning annular recess 211 as examples, when the insertion connecting cap 20 is fixed on the upper area of the connecting seat 10, the positioning annular recess 211 of the outer periphery of the annular connecting portion 21 can engaged with and fixed on the inner periphery of the hollow 11, or the outer screw thread of the outer periphery of the annular connecting portion 21 can be mutually locked with and fixed on the inner screw thread of the inner periphery of the hollow 11. And after the insertion connecting cap 20 is fixed on the connecting seat 10, the bottom end of the connecting portion 21 is pressed against the upper area of the fixed sheet 31 of the elastic valve plug 30 to render the fixed sheet 31 to be positioned against moving.

Figure 5:
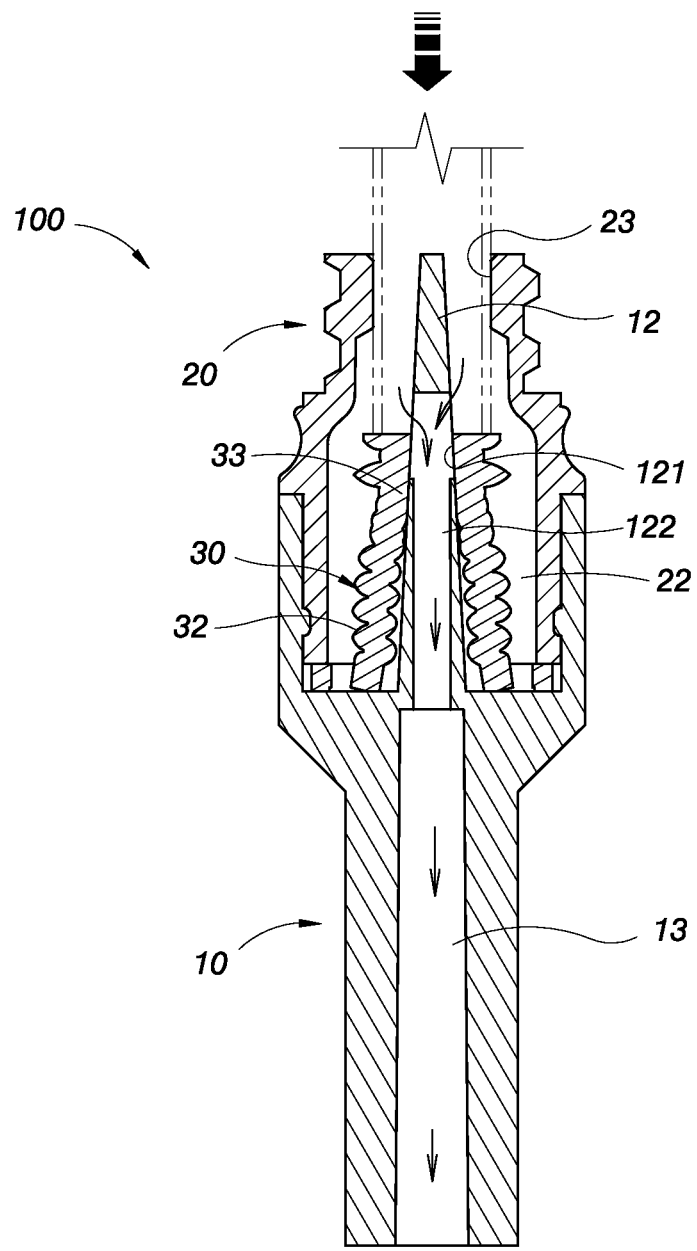
FIG. 5 is a schematic sectional view of the present invention showing the flowing direction of medicament when a needless injection cylinder is inserted into an insertion connecting cap.

As shown in FIG. 5, with the above structure; after the needless injection cylinder is inserted into the injection port 23 of the insertion connecting cap 20, it can squeeze the elastic valve plug 30, to make the sealed portion 33 of the elastic valve plug 30 press the pressed portion 32 downwards to reveal the opening 121 of the conical shaped syringe needle 12, thus the needless injection cylinder can get through the opening 121, the transmitting channel 122 and the pipe connecting terminal 13, to make out putting from the transmitting pipe or absorbing the medicament, air or specimen.

Figure 6:
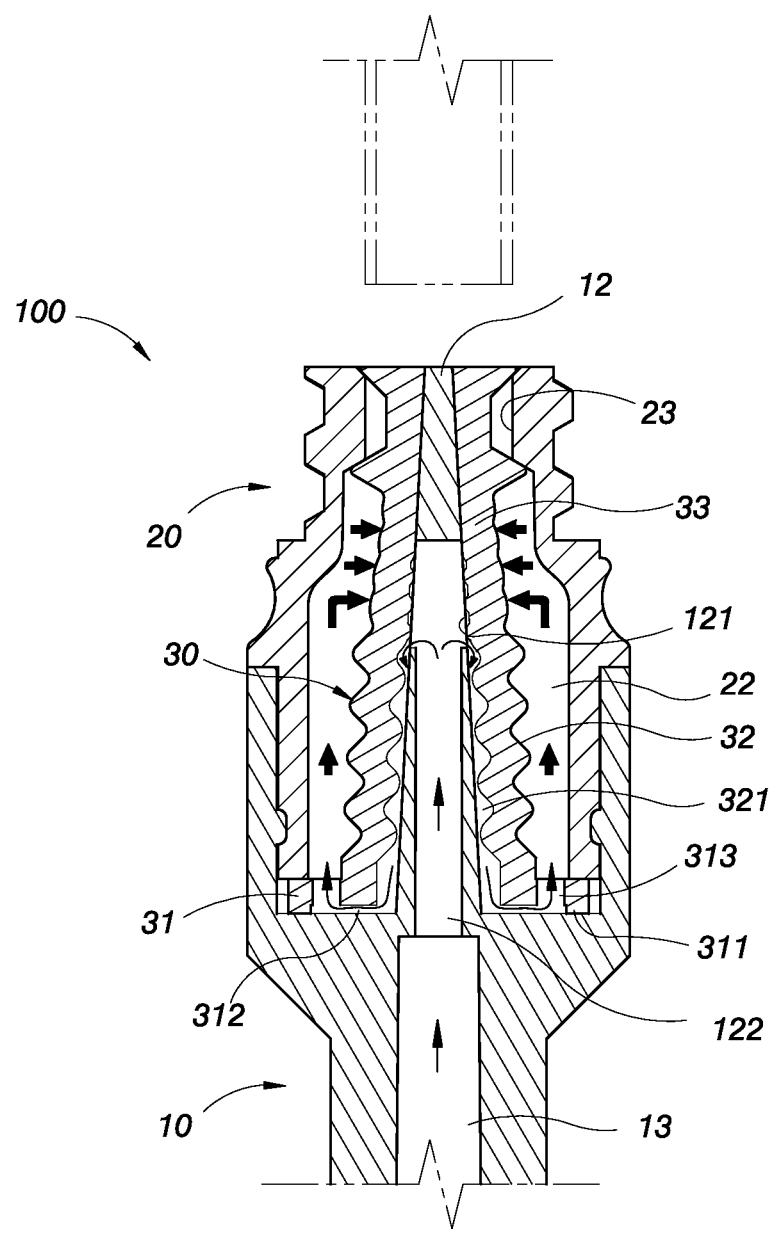
FIG. 6 is a schematic sectional view of the present invention showing the flowing of air of reverse pressure of a connecting seat impeded when an elastic valve plug is restored to its original position.

As shown in FIG. 6, when the needless injection cylinder is pulled out of the injection port 23, the elastic valve plug 30 can restore to its original position, meantime, the reverse pressure generated by the pipe connecting terminal 13 of the connecting seat 10 can get through the transmitting channel 122, the opening 121, the first gap 321, the second gap 312 and the through holes 313, after that, it enters the cavity 22 of the insertion connecting cap 20 to increase the inner pressure of the cavity 22, and then to presses the sealed portion 33 of the elastic valve plug 30 to tightly nestle to the outer periphery of the conical shaped syringe needle 12 to resist the reverse pressure, to avoid contrary flowing of blood or medicament, for the purpose of getting the object of generating better air tight effect with least components.

Figure 7:
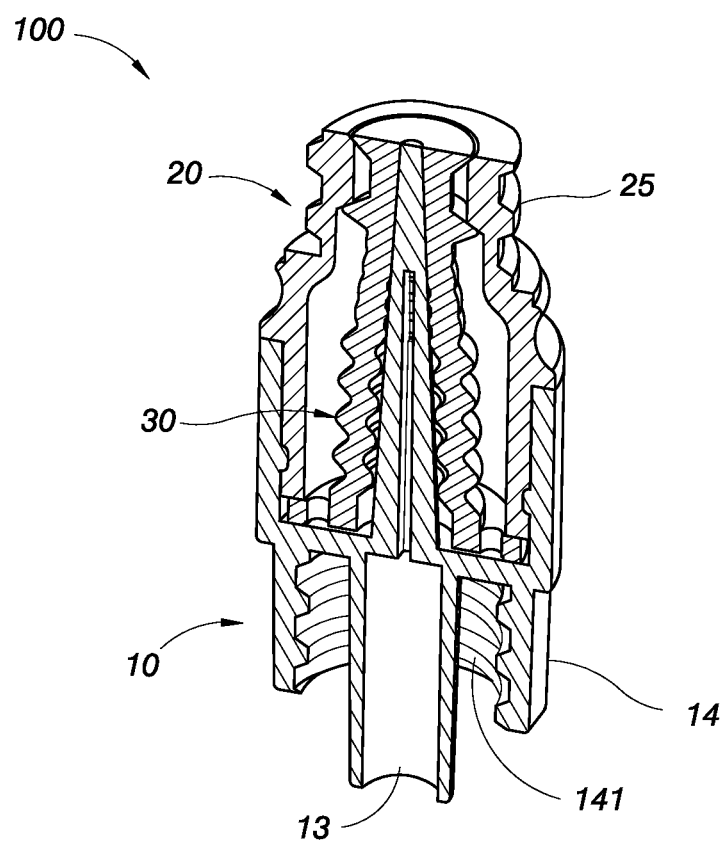
FIG. 7 is a second embodiment of the present invention.

As shown in FIG. 7, the insertion connecting cap 20 is provided on the outer periphery of its top with external screw threads 25, the outer periphery of the connecting seat 10 is provided around the outer wall of the pipe connecting terminal 13 with a fixed wall 14, the inner periphery of the fixed wall 14 is provided with inner screw threads 141; by providing of the external screw threads 25 and the inner screw threads 141, the insertion connecting cap 20 and the connecting seat 10 can do thread connecting with other medical equipments having inner, external screw threads 25 for being stable against moving.

Figure 8:
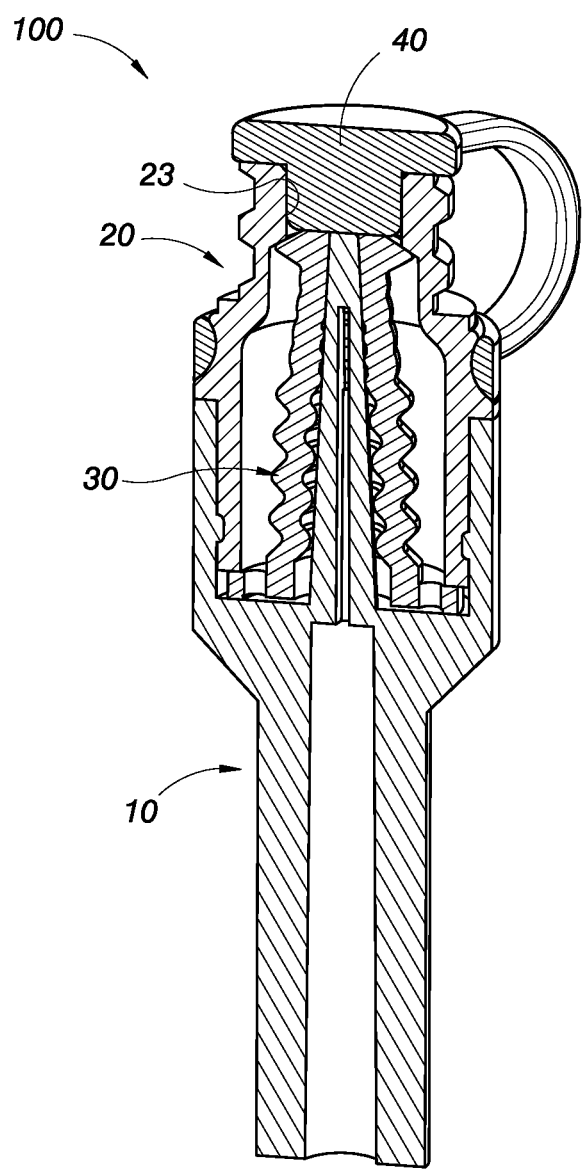
FIG. 8 is a third embodiment of the present invention.

As shown in FIG. 8, the connecting seat 10 further is provided with an obscuring cap 40 for covering the injection port 23, in order to avoid entering of dust, germs into the connector 100.

Figure 9:
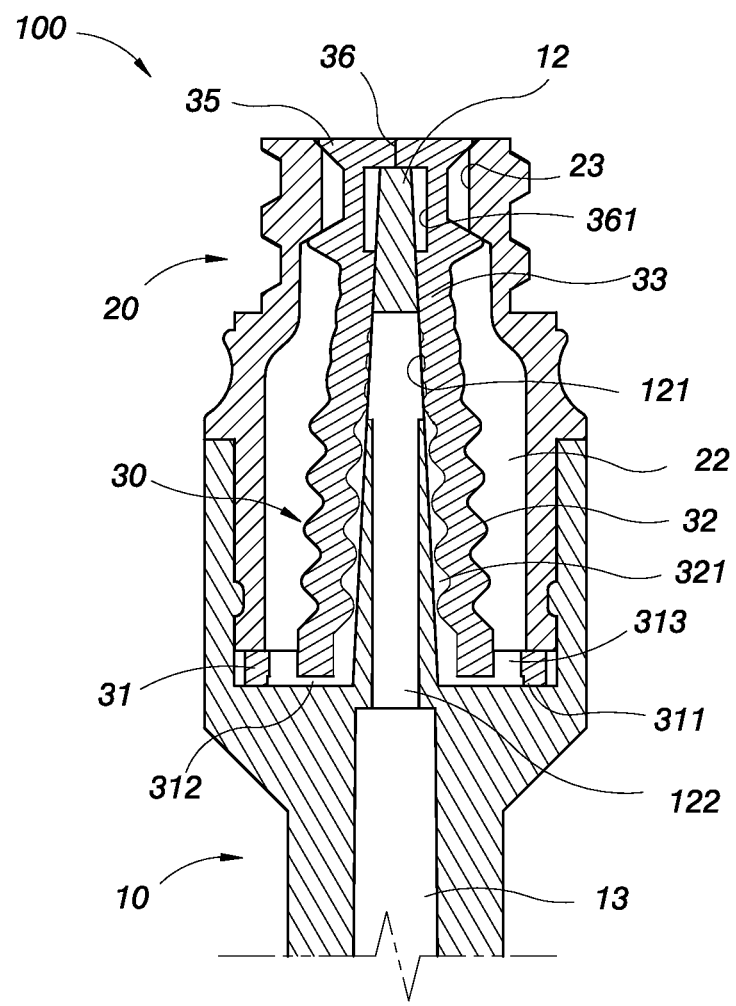
FIG. 9 is a forth embodiment of the present invention.
Figure 10:
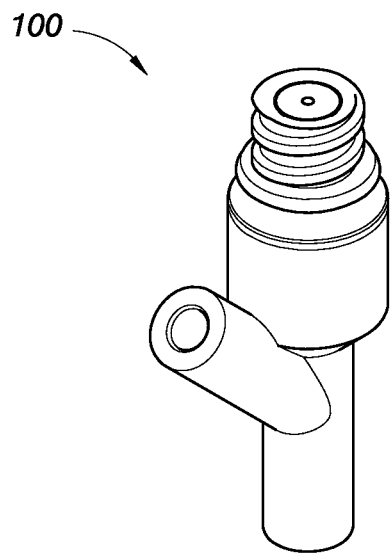
FIG. 10 is a perspective view of a three-way pipe used in the present invention.
Figure 11:
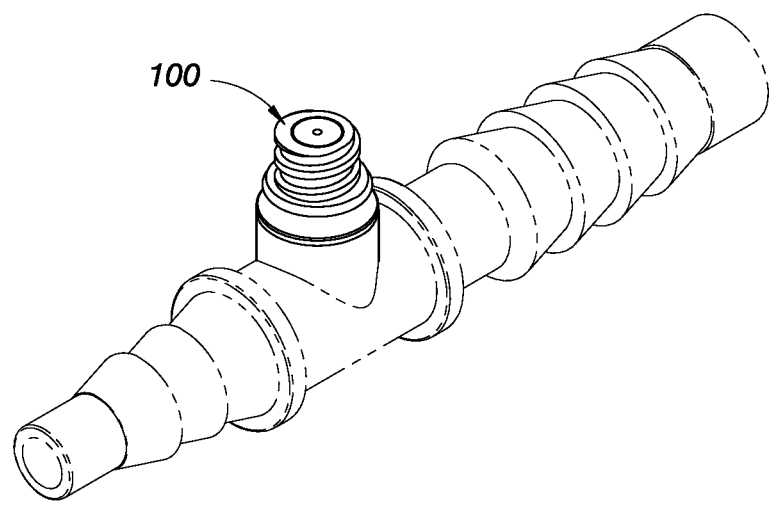
FIG. 11 is a perspective view of another three-way pipe used in the present invention.
Figure 12:
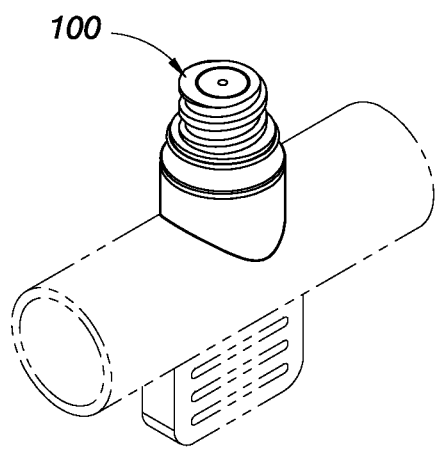
FIG. 12 is a schematic perspective view showing that the present invention is provided on a sampling pipe line of a specimen.

As shown in FIG. 9 which shows another practical example of the elastic valve plug 30, the elastic valve plug 30 covers the conical shaped syringe needle 12 and obscures the top surface of the conical shaped syringe needle 12, the elastic valve plug 30 has a normally sealed narrow seam 36 at a position corresponding to that of the top surface of the conical shaped syringe needle 12, the sealed portion 33 is provided under the sealed narrow seam 36 and at the outer periphery of the top side wall of the conical shaped syringe needle 12 with a buffering gap 361; when the needless injection cylinder is inserted into the injection port 23 of the insertion connecting cap 20, it can squeeze the elastic valve plug 30, to have the second stop annulus 35 been pressed downwards from the buffering gap 361, so that the opening 121 of the conical shaped syringe needle 12 can be revealed from the sealed narrow seam 36 to output or absorb the medicament, air or specimen; after the needless injection cylinder is to be pulled out of the injection port 23 for restoring of the elastic valve plug 30 to its original position, and the sealed narrow seam 36 is to its original position too to be in a normally sealed state, to avoid entering of dust, germs into the connector 100.

Figure 13:
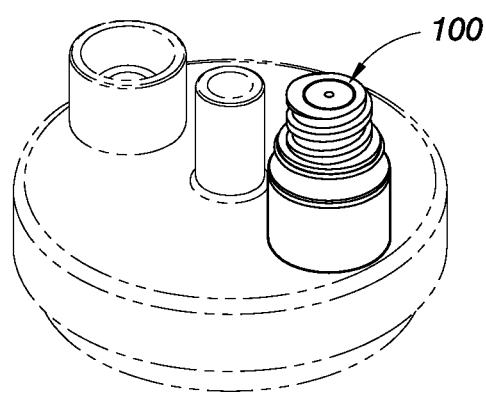
FIG. 13 is a schematic perspective view showing that the present invention is provided on an upper lid of a liquid transmission measuring cylinder.
Figure 14:
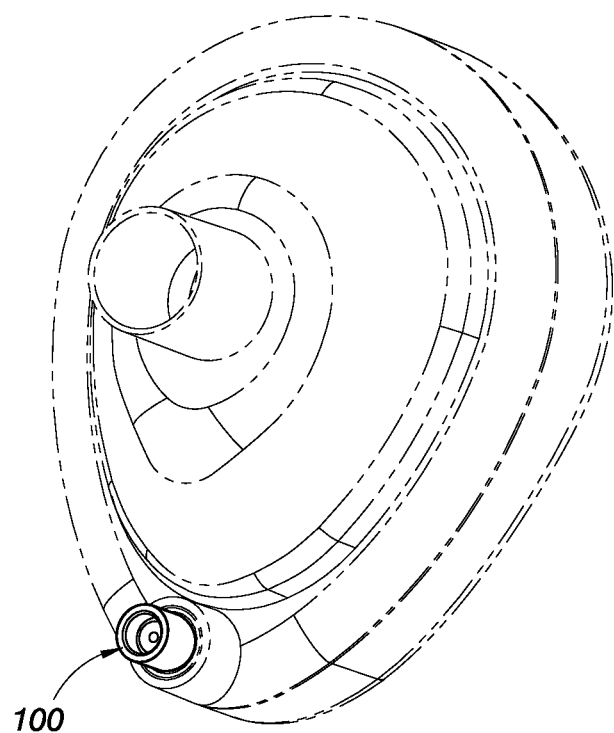
FIG. 14 is a schematic perspective view showing that the present invention is provided on a respirator.

As shown in FIGS. 10 to 14, the connector 100 can be in various forms or can be used for various medical treatments in different circumstances. For example in FIGS. 10, 11, the connector 100 is in the form of a three-way pipe; or in FIG. 12, the connector 100 is installed on a specimen sampling pipe line; or as shown in FIG. 13, the connector 100 is installed on an upper lid of the liquid transmission measuring cylinder; or as shown in FIG. 14, the connector 100 is installed on an air inflation type respirator.

The above stated embodiments and drawings are only for explaining the present invention, not for giving any limitation to the scope of the present invention. It will be apparent to those skilled in this art that various equivalent modifications or changes made to the present invention without departing from the spirit of this invention shall fall within the scope of the appended claims.

The invention claimed is:

1. A connector for medical treatment preventing reverse flow, said connector includes:
    a connecting seat, said connecting seat has a hollow on its top, said hollow has at its center a conical shaped syringe needle, which upwardly protrudes, and said lower area of said hollow is extended downwardly to form a pipe connecting terminal to connect with a transmitting pipe; a top lateral wall of said conical shaped syringe needle is provided at least with an open hole, and has in it a transmitting channel extending downwards through a bottom of said pipe connecting terminal;
    an elastic valve plug in a conical shape covering said conical shaped syringe needle, said elastic valve plug includes a fixed sheet provided at a bottom of said hollow, a pressed portion in a shape having continuous waves extended upwards from said fixed sheet and surrounding periphery of said conical shaped syringe needle, a sealed portion extended upwards from said pressed portion and tightly contact a top outer periphery of said conical shaped syringe needle, a first stop annulus provided on an outer periphery of said sealed portion having an outer radius larger than that of said sealed portion;

an insertion connecting cap fixed on an upper portion of said connecting seat, said insertion connecting cap has an annular connecting portion engaged with an inner periphery of said hollow of said connecting seat, a cavity for placing therein of said conical shaped syringe needle and being provided on an inner periphery of said annular connecting portion, said insertion connecting cap is provided on its top with an injection port connecting with said cavity, a radius of said injection port is smaller than that of said cavity and is provided with a stop wall at a mutual crossing area with said cavity, said first stop annulus of said elastic valve plug is abutted against said stop wall to get an air tight state;

after a needless injection cylinder is inserted into said injection port of said insertion connecting cap, it squeezes said elastic valve plug to make said sealed portion of said elastic valve plug press said pressed portion downwards to reveal an opening of said injection port, thus said needless injection cylinder is adapted to get through said opening, said transmitting channel and said pipe connecting terminal, to output from said transmitting pipe or absorbing medicament, air or specimen;

said inner periphery of said elastic valve plug and said outer periphery of said conical shaped syringe needle have between them a first gap, a bottom of said fixed sheet is provided around it with a downwardly protruding flange, thereby a second gap is formed between a center of said fixed sheet and said hollow of said connecting seat to connect with said first gap, and said fixed sheet is provided thereon with at least one through hole making communication between said second gap and said cavity; said needless injection cylinder is to be pulled out of said injection port for restoring of said elastic valve plug to its original position, a reverse pressure generated by said pipe connecting terminal of said connecting seat is adapted to communicate through said transmitting channel, said open hole, said first gap, said second gap and said at least one through hole, after that, said reverse pressure enters said cavity of said insertion connecting cap to increase inner pressure of said cavity, and then presses said sealed portion of said elastic valve plug to tightly nestle to said outer periphery of said conical shaped syringe needle to resist said reverse pressure.

2. The connector as stated in claim 1, wherein said sealed portion of said elastic valve plug is provided with a second stop annulus corresponding by position to an inner periphery of said opening of said injection port and having a radius larger than that of said sealed portion.

3. The connector as stated in claim 2, wherein said elastic valve plug covers said conical shaped syringe needle and obscures a top surface of said conical shaped syringe needle, said elastic valve plug has a normally sealed narrow seam at a position corresponding to that of said top surface of said conical shaped syringe needle, said sealed portion is provided under said sealed narrow seam and at an outer periphery of said top side wall of said conical shaped syringe needle with a buffering gap; when said needless injection cylinder is inserted into said injection port of said insertion connecting cap, it is adapted to squeeze said elastic valve plug, to have said second stop annulus been pressed downwards from said buffering gap, so that said open hole of said conical shaped syringe needle is adapted to be revealed from said sealed narrow seam to output or absorb medicament, air or specimen.

4. The connector as stated in claim 3, wherein an outer periphery of said connecting seat is provided around an outer wall of said pipe connecting terminal with a fixed wall, an inner periphery of said fixed wall is provided with inner screw threads.

5. The connector as stated in claim 3, wherein said connecting seat further is provided with an obscuring cap for covering said injection port.

6. The connector as stated in claim 3, wherein said insertion connecting cap is provided on an outer periphery of said annular connecting portion with a positioning annular recess or an external screw thread, said inner periphery of said hollow of said connecting seat is provided at a position corresponding to that of said positioning annular recess or an outer screw thread with a positioning protruding annulus or an inner screw thread; said positioning annular recess of said outer periphery of said annular connecting portion of said insertion connecting cap is adapted to be engaged with and fixed on said inner periphery of said hollow, or said outer screw thread of said outer periphery of said annular connecting portion is adapted to be mutually locked with and fixed on an inner screw thread of said inner periphery of said hollow.

7. The connector as stated in claim 6, wherein a bottom end of said connecting portion of said insertion connecting cap is pressed against an upper area of said fixed sheet of said elastic valve plug, said insertion connecting cap is provided on an outer periphery of its top with external screw threads.

8. The connector as stated in claim 7, wherein an outer periphery of said connecting seat is provided around an outer wall of said pipe connecting terminal with a fixed wall, an inner periphery of said fixed wall is provided with inner screw threads.

9. The connector as stated in claim 7, wherein said connecting seat further is provided with an obscuring cap for covering said injection port.

* * * * *